United States Patent [19]

Dassa et al.

[11] Patent Number: 5,279,597
[45] Date of Patent: Jan. 18, 1994

[54] CATHETER COMPRESSION CLAMP

[75] Inventors: Alyssa J. Dassa, Shillington; Raymond K. Newswanger, Terre Hill, both of Pa.

[73] Assignee: Arrow International Investment Corp., Wilmington, Del.

[21] Appl. No.: 819,323

[22] Filed: Jan. 13, 1992

[51] Int. Cl.⁵ .................................. A61M 25/00
[52] U.S. Cl. ........................... 604/283; 604/165; 604/256; 604/163; 285/339
[58] Field of Search ................. 604/163, 165, 171, 240-243, 604/250, 256, 283, 905; 251/7; 285/104, 39, 343

[56] References Cited

U.S. PATENT DOCUMENTS

| | | | |
|---|---|---|---|
| 3,487,837 | 1/1970 | Petersen | 128/349 |
| 3,752,510 | 8/1973 | Windischman et al. | 285/334.4 |
| 3,876,234 | 4/1975 | Harms | 285/38 |
| 3,920,215 | 11/1975 | Knauf | 251/7 |
| 4,013,310 | 3/1977 | Dye | 285/110 |
| 4,116,196 | 9/1978 | Kaplan et al. | 128/272.3 |
| 4,170,995 | 10/1979 | Levine et al. | 128/346 |
| 4,187,848 | 2/1980 | Taylor | 128/347 |
| 4,254,773 | 3/1981 | Waldbillig | 128/348 |
| 4,266,815 | 5/1981 | Cross | 285/330 |
| 4,296,949 | 11/1981 | Muetterties | 285/18 |
| 4,360,025 | 11/1982 | Edwards | 604/180 |
| 4,378,013 | 3/1983 | LeFevre | 251/7 |
| 4,405,163 | 9/1983 | Voges et al. | 285/305 |
| 4,429,852 | 2/1984 | Tersteegen | 251/9 |
| 4,485,014 | 11/1984 | Gilroy et al. | 210/433.2 |
| 4,559,043 | 12/1985 | Whitehouse et al. | 604/201 |
| 4,573,978 | 3/1986 | Reilly | 604/240 |
| 4,583,976 | 4/1986 | Ferguson | 604/174 |
| 4,613,329 | 9/1986 | Bodicky | 604/163 |
| 4,699,616 | 10/1987 | Nowak et al. | 604/180 |
| 4,702,736 | 10/1987 | Kalt et al. | 604/180 |
| 4,704,177 | 11/1987 | Vaillancourt | 156/226 |
| 4,772,276 | 9/1988 | Wiita et al. | 604/283 |
| 4,778,447 | 10/1988 | Velde et al. | 604/29 |
| 4,785,858 | 11/1988 | Valentini et al. | 141/27 |
| 4,792,330 | 12/1988 | Lazarus et al. | 604/174 |
| 4,795,431 | 1/1989 | Walling | 604/97 |
| 4,796,615 | 1/1989 | Bullock et al. | 128/202.27 |
| 4,826,477 | 5/1989 | Adams | 604/4 |
| 4,826,486 | 5/1989 | Palsrok et al. | 604/174 |
| 4,834,719 | 5/1989 | Arenas | 604/174 |
| 4,838,878 | 6/1989 | Kalt et al. | 604/180 |
| 4,842,592 | 6/1989 | Caggiani et al. | 604/283 |
| 4,890,626 | 1/1990 | Wang | 128/752 |
| 4,895,570 | 1/1990 | Larkin | 604/411 |
| 4,919,654 | 4/1990 | Kalt | 604/180 |
| 4,929,236 | 5/1990 | Sampson | 604/175 |
| 4,950,260 | 8/1990 | Bonaldo | 604/283 |
| 5,127,626 | 7/1992 | Hilel et al. | 604/167 |

*Primary Examiner*—John D. Yasko
*Assistant Examiner*—Anthony Gutowski
*Attorney, Agent, or Firm*—Synnestvedt & Lechner

[57] ABSTRACT

A catheter clamp. The clamp comprises a snap-acting device which contains a rotatable inner and outer member. The inner member has an inner passageway for a catheter and an outer surface containing at least one protrusion. The outer member has an interior beveled sidewall. When the outer member is twisted or rotated in a first direction relative to the inner member, the protrusion on the inner member is compressed by the beveled sidewall, thereby compressing the inner member and the catheter. When the outer member is twisted in the opposite direction relative to the inner member, the protrusion disengages from the beveled sidewall and the catheter is decompressed. Use of the clamp in conjunction with a catheter contamination sleeve is disclosed.

11 Claims, 3 Drawing Sheets

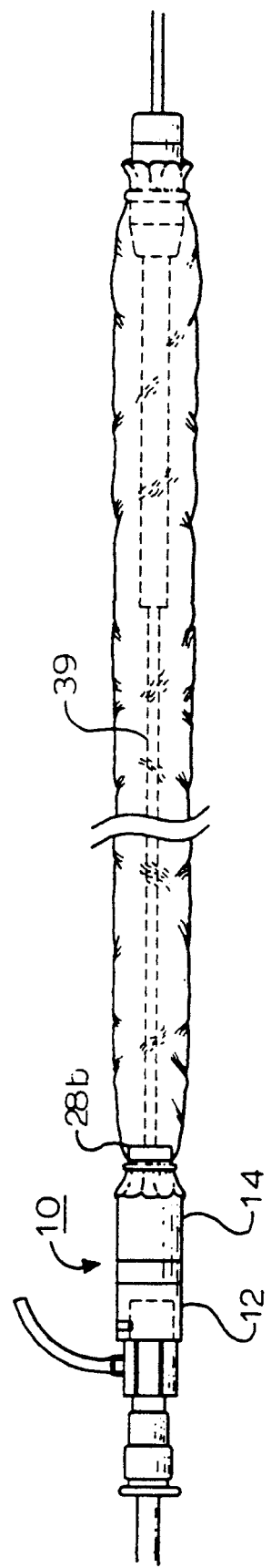

CATHETER COMPRESSION CLAMP

FIELD OF THE INVENTION

The present invention is directed to devices for clamping securely and holding catheters in a fixed position within a patient. In particular, the present invention is specifically directed to a non-rotational catheter clamp which can be easily affixed and adjusted on a catheter.

BACKGROUND OF THE INVENTION

Numerous medical and surgical procedures require catheterization. The catheters utilized for such procedures must be rapidly clamped upon insertion so that they are held in a predetermined fixed position and must therefor be easily adjusted. Numerous types of catheter holders have been proposed by those skilled in the art. Presently, the varieties of catheter holders range from the use of the simple expedient of adhesive tape wrapped around a patient's limb and over a catheter tube to more sophisticated mechanical devices.

Tape arrangements have obvious drawbacks in that they are irritating to the skin of the patient, time consuming to apply and remove, and do not always secure the catheter. Adhesive tapes often fail to prevent a catheter from rotating. The adhesive portion of the tape may also cause a physical-chemical degradation of the catheter tube. Further, tapes are easily contaminated by micro organisms, etc. and cannot be easily cleaned.

Prior art mechanical catheter clamps have typically been cumbersome and have often included complex mechanical parts which may impede the flow of fluids through the retained or clamped catheter. Many prior art catheter clamps deform the catheters with which they are used and often utilize complex attachment means. Such catheter clamps are difficult to quickly move and maneuver. Further, a number of prior art clamps rely upon adhesives for purposes of securing the catheter to the patient. Such adhesives tend to lose their gripping ability after the catheter is turned or twisted, and often have the above discussed problems associated with adhesive tapes.

A number of patents have highlighted the types of problems associated with prior art mechanical catheter clamps. U.S. Pat. No. 4,360,025 discloses a catheter clamp constructed from a plastic material having a central hole which is fully or partly defined by a pair of resilient catheter-gripping serrated jaws and a resilient catch member for holding the jaws in their relatively closed position. The serrated jaws of this clamp may have a tendency to dig into or deform the catheter. Further, the arrangement requires that the catheter enter the body substantially perpendicularly to the skin surface.

U.S. Pat. No. 4,699,616 discloses a device for retaining a drainage catheter in place at its point of entry into a patient's body at an attitude which is perpendicular to the skin surface. The device includes a resilient, adhesive barrier pad having an opening intended to be aligned with the fenestration in the body wall. The pad has an entry slit leading to the opening. In use, the catheter is guided laterally through the entry slit to the opening of the barrier pad and then supported by mechanical support arms which may deform the catheter. The resilient pad is then adhesively secured to the patient with the edges of the pad defining a slit urged tightly together.

U.S. Pat. No. 3,487,837 discloses a mechanism for retaining a catheter in position such that the catheter is frictionally gripped by the taper in a bell shaped elastic body. The elastic body has a narrow neck for forming a walled sleeve about the catheter, and the cavity is formed in the wall inwardly of the sleeve. Any tendency of the catheter to move outward causes the sleeve to stretch and resist this movement.

U.S. Pat. No. 4,170,995 discloses a holder for clamping a catheter or other hollow tube. The holder comprises a pliant adhesive base which is adhered to the patient's skin. The holder is adjustable so as to be securer against rotary and longitudinal movement. The device also incorporates a screw and nut configuration which is comparatively difficult to quickly affix and adjust. The device deforms the catheter in use and is adjustable to completely cut off flow.

U.S. Pat. No. 4,702,736 discloses a clamp for holding an article such as a catheter. The device includes a series of folding flaps comprising resilient adhesive surfaces. These surfaces adhere the catheter to the base of the clamp.

Finally, U.S. Pat. No. 4,842,592 discloses an adaptive connector assembly for engaging a catheter. The invention comprises a pair of segments adapted for telescoping engagement so as to provide a central cavity for receiving a plug of compressible material. One of the segments has an opening which communicates with the cavity and is adapted to receive the catheter. The plug has a centrally disposed channel for receiving the catheter from the opening. A snap-fit engagement is developed between the telescoping segments so that when the telescoping segments are engaged, the plug is placed in compression, constricting the channel about the catheter and thereby engaging the catheter within the adaptive connector assembly. This device is comparatively complex and includes a number of parts, including a separate plug which must be properly positioned for use.

There have also been a number of prior art patents directed to adaptors for connecting a catheter to a syringe. None of these devices discloses or suggests the catheter clamp of the present invention. U.S. Pat. No. 3,752,510 discloses a connector structure for connecting a flexible tube to a syringe having a luer tip. The patent utilizes a construction in which a retainer and tube end are urged into a tapered bore.

U.S. Pat. No. 4,834,719 discloses a quick connect/disconnect tubing adapter with locking mechanism for capturing a tube within the adapter. The adapter comprises two mating body portions having passageways for receiving a tubing end portion. Each of the above methods and devices for clamping a catheter is cumbersome, and makes the catheter difficult to attach quickly and to easily decouple. It is often important to rapidly affix and adjust a catheter into position. This is particularly difficult with clamps such as disclosed in U.S. Pat. No. 4,360,025. In addition, clamps incorporating the use of adhesives, such as disclosed in U.S. Pat. No. 4,170,995, do not always adequately secure the catheter and present the previously discussed problems associated with adhesives.

It would be desirable to have a device for clamping a catheter which can be quickly clamped and unclamped. It would be particularly desirable to have a catheter clamp which can be easily clamped and unclamped with a single twisting movement. Such a clamping device could be quickly attached to a catheter without the need for adhesives.

It is accordingly an object of the present invention to provide a non-rotational catheter clamp which can be rapidly attached and released for repeated use.

It is still a further object of the present invention to provide a snap acting non-rotational catheter clamp which can be rapidly and easily attached and decoupled by a single twisting movement.

It is still yet a further object of the present invention to provide a snap acting catheter clamp which can be attached and adjusted without deforming the catheter with which it is utilized and without the need for adhesives.

It is an additional object of the present invention to provide a catheter clamp which can secure catheters having a variety of diameters.

It is a further object of the present invention to provide a catheter clamp which could be utilized for controlling the adjustment of a catheter such as disclosed in U.S. Pat. No. 4,327,723. The inclusion of the clamp of the present invention is uniquely suited for connection to the protective sheath of a shielded catheter such as disclosed in U.S. Pat. No. 4,327,732 in that it allows for periodic readjustment and clamping of the catheter in a readjusted position without risk of catheter sepsis.

These and other objects of the present invention will become apparent from the Summary and Detailed Description which follow.

SUMMARY OF THE INVENTION

In accordance with the present invention, a non-rotational catheter clamp is disclosed. The catheter clamp of the present invention facilitates the rapid clamping and release of a catheter, without deforming the catheter with which it is used. The disclosed clamp comprises a first compressible inner member having a central passageway for a catheter and an outer wall containing a protrusion; a second outer member in rotatable contact with said first compressible inner member and having an interior beveled surface which is rotatably matable with said protrusion such that when said first inner member is rotated in a first direction relative to said second outer member, said protrusion rotates toward and is compressed inwardly by said interior beveled surface, thereby compressing said first inner member and said central passageway, and when said compressed first inner member is rotated in a second direction relative to said second outer member, said protrusion rotates away from said interior beveled surface thereby decompressing said inner member and said passageway.

In a more preferred embodiment, the disclosed catheter clamp comprises a first inner substantially cylindrical member having a passageway for a catheter and containing an outer surface having at least one rib-like protrusion; a second coaxial outer member rotatably matable with said first inner member and having a beveled interior sidewall, said rib-like protrusion being rotatably matable with the interior sidewall of the outer member so as to depress said rib-like protrusion and compress said inner member and passageway when said outer member is rotated in a first direction relative to said inner member, and so as to decompress said compressed inner member and passageway when said outer member is rotated in a second direction relative to said first member. The catheter clamp of the present invention includes means for limiting the rotation of the clamp.

BRIEF DESCRIPTION OF THE FIGURES

FIG. 6 is a perspective view of a catheter insertion system using the snap-lock clamp of the present invention.

DETAIL DESCRIPTION OF THE PREFERRED EMBODIMENT

Figure 1:
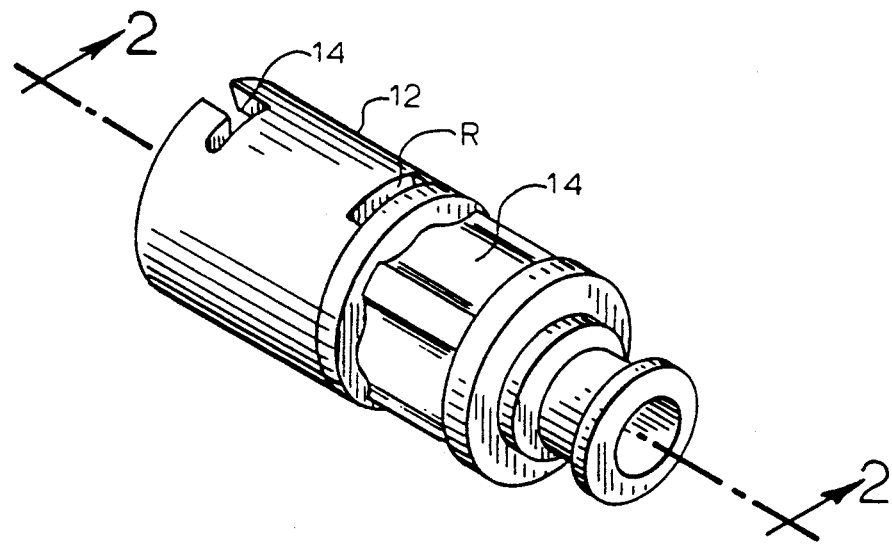
FIG. 1 is a perspective view of the snap lock catheter clamp of the present invention.
Figure 5:
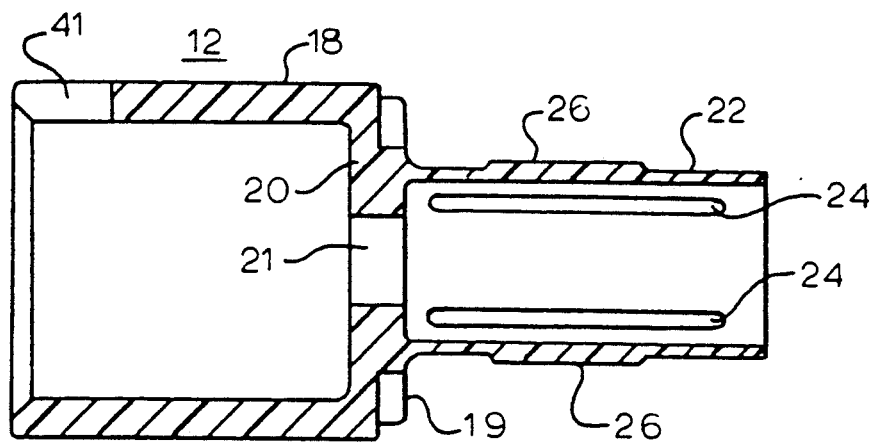
FIG. 5 is a partial section view of the inner compressible member of the present invention.

The present invention is described with reference to the enclosed Figures wherein the same numbers are utilized where applicable. Referring to FIGS. 1 and 5, the snap-acting non-rotational catheter clamp 10 of the present invention comprises two rotatably matable, members 12 and 14. The term "non-rotational" as used herein refers to a catheter clamp that does not rotate relative to the catheter with which it is used. Member 12 is a hollow cylindrical member which has a large diameter first end portion 18 and which is joined by a central wall 20 portion to a second, smaller diameter hollow cylindrical end portion 22. The exterior surface of wall section 20 further creates an exterior mating wall surface 19. Central wall catheter to extend between first and second hollow ends 18, 22. As more clearly shown in FIGS. 3a and 5, the surface of second end portion 22 contains longitudinally extending slits 24 and four rib-like protrusions 26 separated at approximate 90 degree intervals about the surface. The relatively thin walled, second end portion allows for radial inward compressibility for reasons explained more fully below.

The second, outer cylindrical member 14 is a composite member and comprises a cylindrical nose piece 28 and cylindrical outer member 30. Nose piece 28 contains an annular ridge 25 about its outer periphery for mating with a groove located internally of the bore in the first end of a second cylindrical outer member 30. Nose piece 28 and outer member 30 are connected together.

The second outer member 30 is coaxial with narrow compressible end 22 and contains an annular foot 31 which rests upon the outer surface of compressible end portion 22. The outside surface 30b of outer member 30 contains a plurality of longitudinal ridges 23 which facilitate gripping. As will be discussed below, the second outer member 30 contains an annular exterior mating wall 33 at its second end which rotatably mates with and lies flush against the exterior mating wall 19 of the larger diameter first end 18 of member 12. While the present invention is being described in the context of cylindrical members, it is to be appreciated by those skilled in the art that the respective members 12, 14 need not be cylindrical but may have a variety of shapes.

The cylindrical nose piece 28 further contains an annular recess 32 which receives and is joined to the end of the second radially yieldable compressible end portion 22. The nose piece 28 rotates relative to the narrow compressible end portion 22 at the annular recess 32. The interior surface of the nose piece 28a is contoured to facilitate connection to a syringe of the type having a plunger with an axial throughbore intended for the insertion of a catheter into a blood vessel of a patient. In addition, the nose piece 28 has a flanged outer end 28b. As will be described below, flanged outer end can be used to secure a protective outer sheath and O-ring to the clamp 10.

Figure 2:
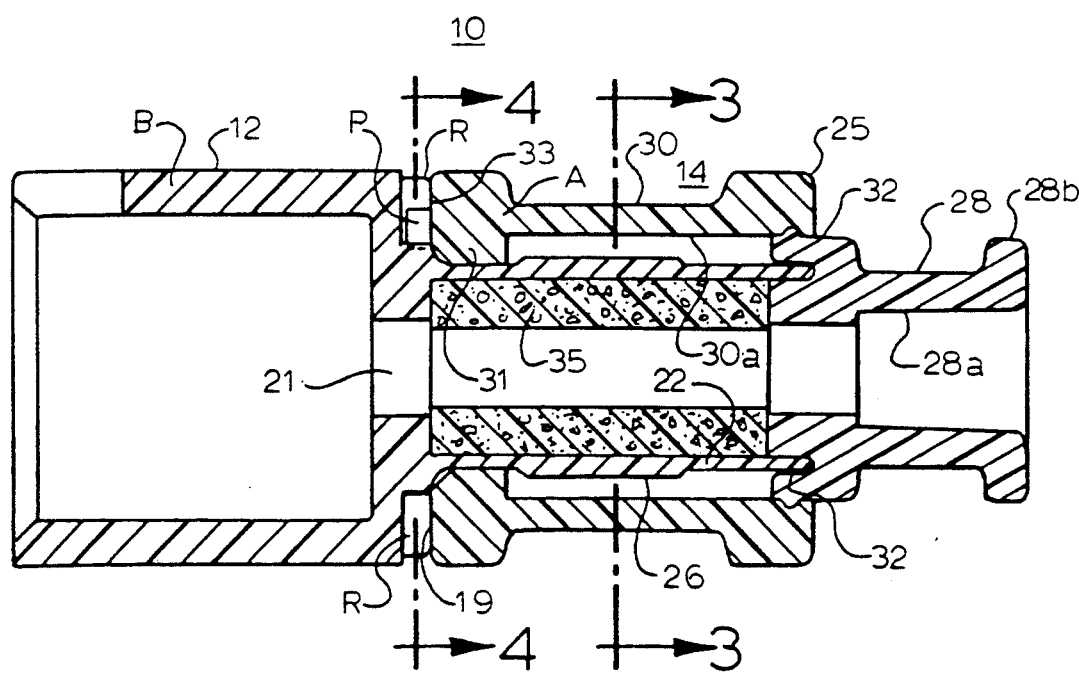
FIG. 2 is a section view of the catheter clamp of the present invention along line 2—2 of FIG. 1.
Figure 3A:
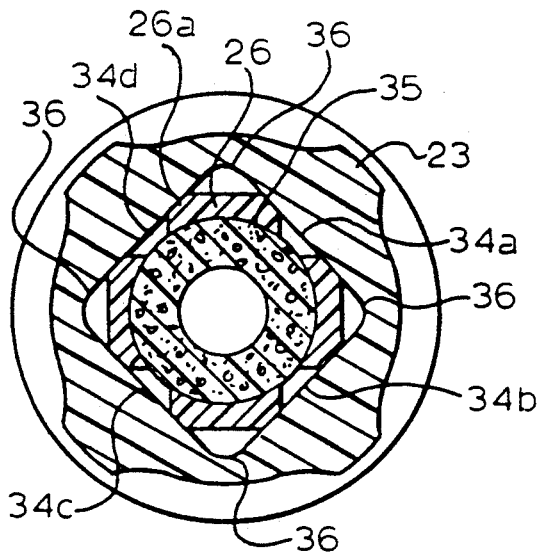
FIG. 3a is a section view of the catheter clamp of the present invention along line 3—3 of FIG. 2 in a decompressed deactivated state.

As noted above, the outer surface of the narrow compressible end portion 22 contains four longitudinally extending rib-like protrusions 26 separated at 90 degree intervals. Referring specifically to FIG. 5, compressible end portion 22 is preferably constructed from a pliable elastomer and contains longitudinally extending slits 24 on opposing sides of each protrusion 26 which, as will be described below, facilitate the even radially inward compression of the protrusions 26. As shown in FIG. 2 and 3a, the interior surface of narrow compressible end 22 is fitted with a cylindrical tubing insert which is preferably a resilient liner 35. Although other resilient materials may be employed, the inclusion of compressible rubber or spongy foam material as the resilient liner 35 is particularly effective in locking the catheter in position and facilitates the use of the clamp 10 with catheters having a range of diameters.

Figure 3B:
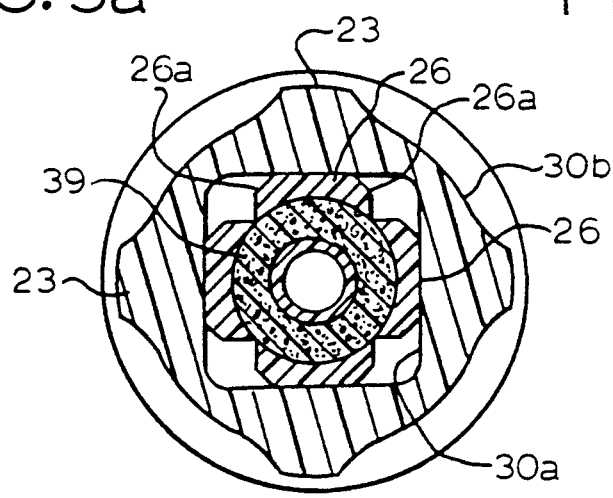
FIG. 3b is a section view of the catheter clamp of the present invention in a compressed activated state.

Referring to FIGS. 3a and 3b, the circumference of the interior surface 30a of outer member 30 is preferably diamond (square) shaped and is defined by four sidewalls 34a-d. In the non-compressed state of end portion 22, the respective four rib-like projections 26 are each situated below a respective one of the four peaks 36 of the four sidewalls 34 of the diamond. The corners of each rib-like protrusion 26 are beveled, as shown at 26a, so as to mate with the opposite sidewalls 34a-d defining a respective diamond peak 36 and so as to prevent the clamp from inadvertently engaging. Referring to FIG. 3b, as the inner rotatable member 12 is rotated at a 45 degree angle relative to the outer member 30, each respective protrusion 26 rotates into and lies flush against a respective interior sidewall 34a-d. The contour of the sidewalls serve as a camming means to press the protrusions 26 inwardly, thus in turn pressing the tube of resilient material 35 radially inwardly. A catheter 39 which is located within the central passageway is thereby compressed and held rigid.

While the preferred embodiment is disclosed in the context of an outer member 30 having diamond (square) shaped interior sidewalls, it is to be appreciated that the internal sidewalls 34 may take other shapes and geometric configurations which achieve at least some of the objectives of the invention. Furthermore, it is to be appreciated that the sidewalls may provide for rotation of more than 45° and may comprise an interior surface having more than four sidewalls. It is specifically envisioned that the sidewalls may have one contour over a first rotatable portion and then change to a more oblique or less oblique contour so as to provide a second surface which alters the compression of the catheter. In this manner, a single clamp could provide multiple levels of compression, and accordingly could be used with catheters having significantly different diameters.

Figure 4:
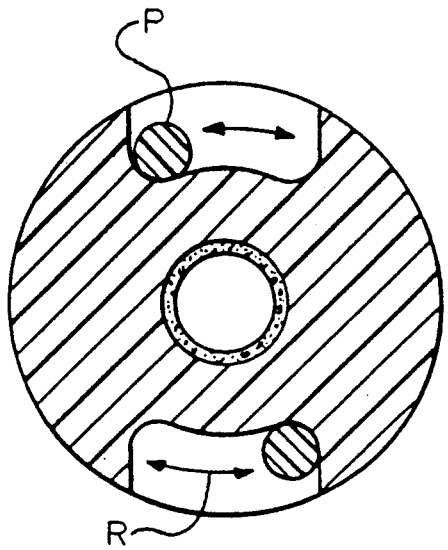
FIG. 4 is a section view which illustrates the stop members of the present invention.

As shown in FIGS. 1, 2 and 4, the catheter clamp of the present invention provides a mechanism for limiting the relative rotation of the members 12 and 14. The exterior mating wall surface 19 of the first end portion 18 of member 12 contains two opposing coaxial recesses designated by the capital letter R. Each recess R circumscribes an arc of approximately 45 degrees on the exterior mating wall 19 of member 18. The adjacent wall 33 of outer member 30 contains axial projecting pins P which mate with and slide within the groves R. The union of pins P within grooves R limits the relative rotation of members 12 and 14 in operation to about 45 degrees as shown by the arrows in FIG. 4. Thus, the clamp 10 can be easily positioned between the open and closed positions as shown in FIGS. 3a and 3b.

The operation of the present invention is now described with reference to all of the Figures. Initially, a catheter 39 is inserted through the middle of the catheter clamp in an open position, as shown in FIG. 3a. The catheter 39 resides unclamped between the resilient liner 35 located within the interior of the compressible end of the inner member 22. The protrusions 26 rest in an uncompressed state below the peaks 36 formed by the diamond (square) shaped interior surface of member 30a. The beveled surfaces 28a mate with the respective opposing sidewalls 34a-d defining a diamond peak and secure the clamp in an open position. As the outer cylindrical member 30 is twisted or turned in a first direction relative to member 12, the rib-like protrusions 26 rotate into a respective sidewall 34 which defines a peak of the diamond. The inclusion of the beveled corners 26a provides the catheter clamp with a snapping action when engaged. As can be seen in FIG. 3b, the inner cylindrical end 22 member is thereby compressed inwardly, facilitated by the slits 24, and thus compresses the resilient liner 35 and locks the catheter 39 in place. Referring to FIG. 4, grooves R and pins P limit the rotation of members 12, 14 of the clamp to about 45 degrees.

With this arrangement, there is no intermediate clamping position. When the parts are in the position of FIG. 3a the catheter is freed for axial movement within the passageway. In the position of FIG. 3b, the protrusions are fully radially compressed and the catheter is clamped. The compressible nature of resilient liner 35 assures that the catheter will not be deformed when it is held in the clamped position.

In order to decompress the catheter clamp and release the catheter 39, the outer cylindrical member 30 is turned in the opposite direction relative to member 12. As each respective sidewall wall 34a-d is turned away in the opposite direction relative to the protrusions 26, the rib-like protrusions 26 align again with the peaks 36 defined by the sidewalls 34a-d. Situated beneath the peaks 36, the rib-like protrusions 26 can completely expand.

The compressed resilient insert 35 accordingly expands and the catheter 39 can then move freely again. It is to be appreciated that the present invention could be utilized with a plurality of insertible resilient liners 35, each having a different diameter. In this way, a plurality of different catheters could be accommodated using a single snap acting clamp 10. The catheter clamp 10 further contains a bayonet coupling 41 to couple the catheter clamp 10 to devices such as the corresponding male coupling of an introducer, adaptor, catheter sleeve, or other implement.

The catheter clamp of the present invention may further be utilized with a catheter advancement system such as disclosed in U.S. Pat. No. 4,327,723, which is incorporated herein by reference as if set forth in full. In such an application, the catheter clamp 10 of the present invention fits between the catheter introducer and the protective catheter sheath and may replace the front hub 21, shown most particularly in FIG. 3 of U.S. Pat. No. 4,327,732 and described at column 3, lines 27-31 and column 4, lines 24-27 of U.S. Pat. 4,327,732. In this embodiment, flanged end 28b secures the transparent protective sheath with an O-ring. Thus, as shown in FIG. 6, (a modified partial view of FIG. 5 of U.S. Pat. No. 4,327,723), using the snap-acting catheter clamp 10 of the present invention, the insertion of a catheter 39, such as a cardiopulmonary balloon tip catheter, can be controlled and locked such that the catheter 39 can be periodically adjusted and clamped in readjusted position. The arrangement of clamp and protective sheath allows for repeated adjustments of catheter position without risk of catheter sepsis and provides positive clamping action so that the catheter position is not inadvertently shifted.

The present invention has been described with reference to the enclosed figures. It is to be appreciated by those skilled in the art, that other embodiments will fulfill the scope of the present of invention and that the true nature and scope of the present invention should be determined with respect to the claims appended hereto.

What is claimed is:

1. A non-rotational catheter clamp comprising:
   a first compressible inner member having an interior passageway for a catheter, an outer surface containing at least one rib-like protrusion and a plurality of slits which facilitate the even compression of said first compressible inner member;
   a second co-axial outer member in rotatable contact with said inner member and having at least one interior sidewall which rotatably compresses said at least one rib-like protrusion when said outer member is rotated in a first direction relative to said first compressible inner member, thereby compressing said inner member and locking a catheter within said passageway, and which rotatably decompresses said rib-like protrusion when said outer member is rotated in a second direction relative to said compressed inner member, thereby decompressing said inner member and unlocking a catheter within said passageway 2. The non-rotational catheter clamp of claim 1 wherein said slits extend longitudinally along the surface of said inner member.

3. The catheter clamp of claim 1 wherein the interior passageway defined by said inner member is lined with a resilient compressible material.

4. The catheter clamp of claim 3 wherein said resilient compressible material is a spongy foam.

5. A non-rotational catheter clamp comprising:
   a first cylindrical hollow inner member containing a central passageway for a catheter and an outer generally flexible wall containing four rib-like protrusions separated at about 90 degree intervals by elongated slits extending lengthwise thereof;
   a second coaxial cylindrical outer member rotatably matable with said inner member and having a plurality of interior surfaces each of which is rotatably matable with one of said protrusions, such that when said first inner member is rotated at about 45 degrees in a first direction relative to said second outer member, each of said protrusions is compressed against a corresponding one of said surfaces, thereby compressing said inner member and said passageway, and such that when said compressed inner member is rotated at about 45 degrees in the opposite direction relative to said second member each of said protrusions is rotated away from each of said corresponding interior surfaces, and said inner member and said passageway decompresses.

6. A non-rotational catheter clamp comprising:
   a first inner member containing a central passageway for compressing and securing a catheter and an outer generally flexible wall having four rib-like protrusions separated at 90 degree intervals;
   a second co-axial outer member rotatably matable with said inner member and having four beveled interior sidewalls, each of which is rotatably matable with one of said rib-like protrusions, such that when said inner member is rotated in a first direction relative to said second member, each of said protrusions is compressed against one of said sidewalls thus compressing said central passageway, and such that when said compressed inner member is rotated in the opposite direction relative to said second outer member each said protrusion is rotated away from each said sidewall and said passageway decompresses; and
   means for limiting the rotation of said first inner and second outer members.

7. The catheter clamp of claim 6 wherein said central passageway is lined with a compressible spongy foam material 8. The catheter clamp of claim 6 wherein said inner member contains a plurality of slits disposed between said protrusions which facilitate the even compression of said inner member about said catheter.

9. The catheter clamp of claim 6 wherein said inner member contains means for connecting the clamp to another implement.

10. The catheter clamp of claim 6 further including a protective catheter sheath disposed in overlying relationship to a length of catheter intended for introduction into a blood vessel of a patient, wherein said outer member contains means for securing said catheter clamp to said protective sheath.

11. A clamp according to claim 9 wherein said implement is a catheter introducer, further including a protective catheter sheath disposed in overlying relationship to a length of catheter intended for introduction into a blood vessel of a patient, wherein said outer member contains means for securing said catheter clamp to said protective sheath.

* * * * *

UNITED STATES PATENT AND TRADEMARK OFFICE
CERTIFICATE OF CORRECTION

PATENT NO. : 5,279,597

DATED : January 18, 1994

INVENTOR(S) : Dassa et al.

It is certified that error appears in the above-identified patent and that said Letters Patent is hereby corrected as shown below:

Column 4, line 38, after "Central wall" insert --section 20 contains a circular aperture 21 for permitting a--.

Signed and Sealed this

Twenty-second Day of November, 1994

Attest:

BRUCE LEHMAN

*Attesting Officer*     *Commissioner of Patents and Trademarks*